United States Patent [19]

Schiffman et al.

[11] Patent Number: 4,768,521
[45] Date of Patent: Sep. 6, 1988

[54] PRESSURE ALGOMETER APPARATUS

[75] Inventors: Eric L. Schiffman; James R. Fricton, both of Minneapolis; Lawrence M. Espy, Edina, all of Minn.

[73] Assignee: Regents of the University of Minnesota, St. Paul, Minn.

[21] Appl. No.: 26,625

[22] Filed: Mar. 17, 1987

[51] Int. Cl.[4] .............................................. A61B 5/10
[52] U.S. Cl. .................................................... 128/774
[58] Field of Search ............... 128/677, 687, 691, 694, 128/744, 774, 782

[56] References Cited

U.S. PATENT DOCUMENTS

| 3,156,237 | 11/1964 | Edmark | 128/687 |
| 4,122,837 | 10/1978 | Leonard | 128/774 |
| 4,250,894 | 2/1981 | Frei et al. | 128/774 |
| 4,337,780 | 7/1982 | Metrick |  |
| 4,338,950 | 7/1982 | Barlow | 128/782 |
| 4,635,506 | 3/1987 | Romanooskaya | 128/687 |

FOREIGN PATENT DOCUMENTS 1185443  3/1970  United Kingdom ................ 128/694

OTHER PUBLICATIONS

"Pain and Soft Tissue Pathology Instruments" from Pain Diagnostics and Thermography (four-page brochure).

Primary Examiner—Max Hindenburg
Attorney, Agent, or Firm—Merchant, Gould, Smith, Edell, Welter & Schmidt

[57] ABSTRACT

A pressure algometer apparatus (20,50). The pressure algometer apparatus (20) provides an all mechanical pressure algometer including a balloon-like bladder member (22) for positioning at an end of a user's finger. An air tight interior (44) of the balloon-like member (22) is interconnected by tubing (42) to a pressure gauge (40). The algometer apparatus (50) includes a handheld pressure transducer (52) electrically interconnected (53) to an amplifier meter arrangement (54).

4 Claims, 2 Drawing Sheets

U.S. Patent  Sep. 6, 1988  Sheet 1 of 2  4,768,521
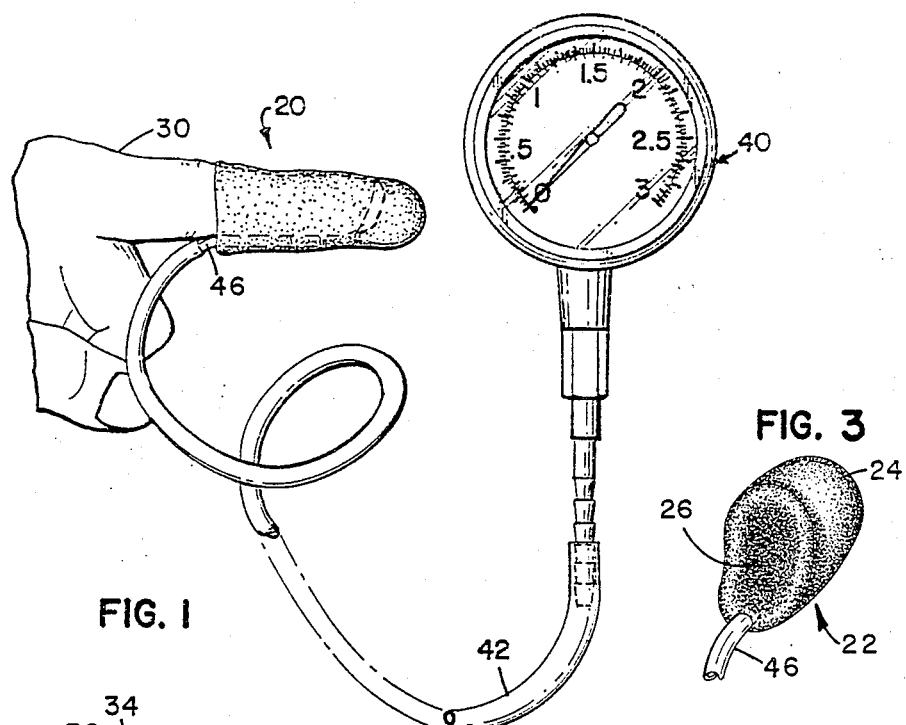
FIG. 1
FIG. 3
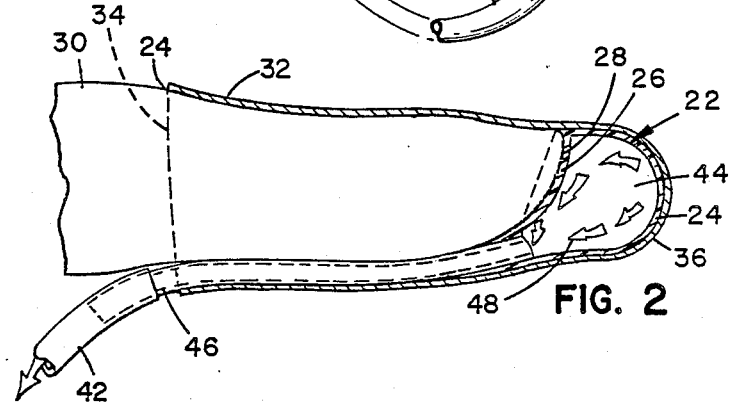
FIG. 2
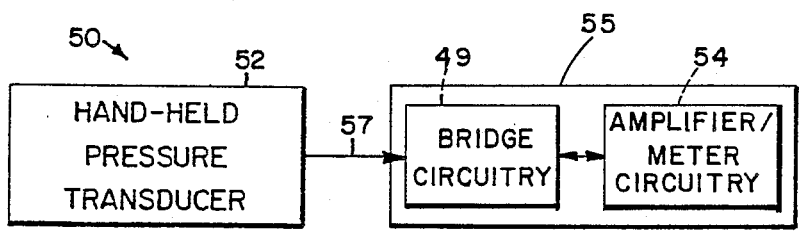
FIG. 4

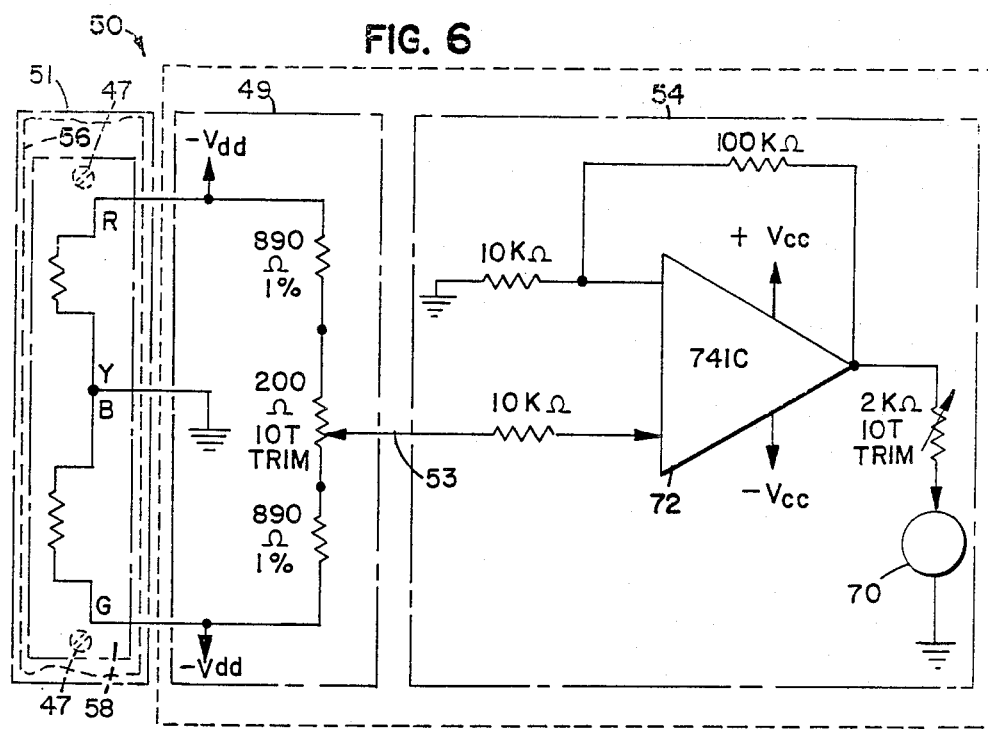
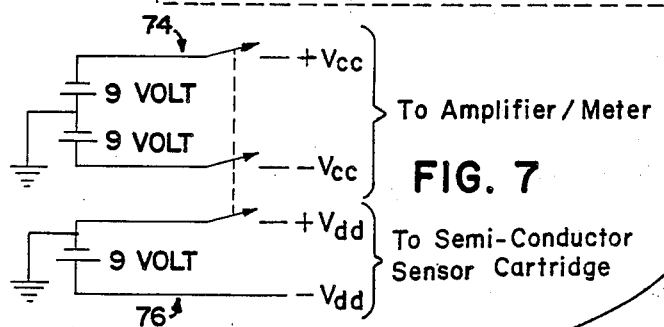
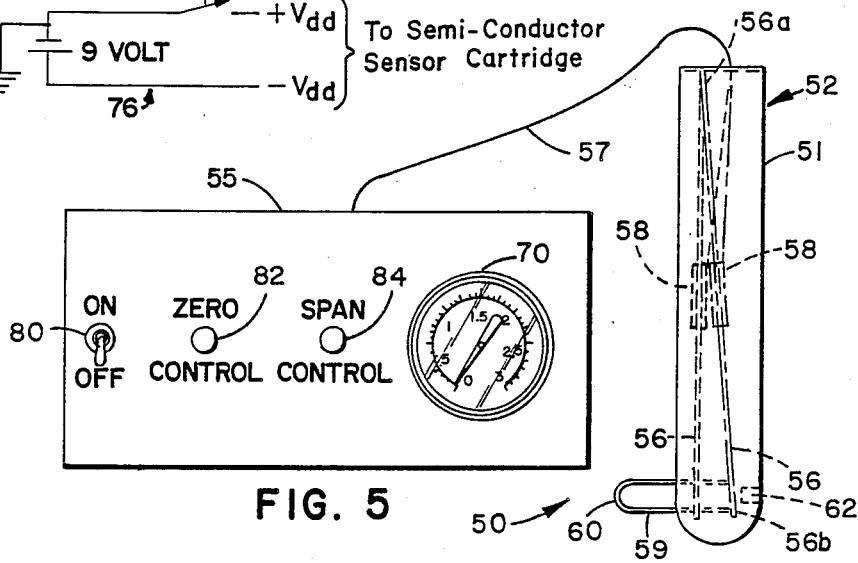

PRESSURE ALGOMETER APPARATUS

BACKGROUND OF THE INVENTION

The present invention relates to a pressure algometer apparatus, and more particularly, to a pressure algometer apparatus for diagnosis of muscle pain or tenderness when subjected to pressure.

Myofascial pain and dysfunction is the most common disorder causing chronic head and neck pain. Traditionally, diagnosis and assessment of the severity of this disorder depends on the tenderness of myofascial tissue at specific locations, often referred to as trigger points, to manual palpation. Manual palpation is accomplished by using one's fingers to apply varying pressure against the trigger points and to observe patient response. However, this technique is often unreliable, due in part to the inability to accurately measure the variation in pressure applied at the trigger point. The present invention solves this and other problems associated with this diagnostic technique.

U.S. Pat. No. 4,337,780 issued to Metrick shows that pressure sensing devices have been used to test muscle strength. The Metrick patent teaches the use of an air tight bag of any suitable configuration depending on the muscle whose strength is to be tested, which is interconnected by tubing to a pressure responsive device so as to form an air tight compartment. The pressure responsive device consists of any suitable device commercially available to measure air pressure, such as a sphygmonanometer. In use, the air tight bag is typically attached to the palm side surface of the distal end of the tester's index finger by an elastic band or the like and/or is attached to the back of the tester's hand.

The Metrick invention is used to test muscle strength and not muscle pain threshold or tenderness. Muscle strength testing devices have long been used. In muscle strength testing, the force applied to the overall muscle is measured. The configuration and consistency of the device used to apply the force is not critical. Therefore, in addition to other differences, there is no teaching or suggestion in Metrick of a pressure sensitive device having a specific configuration and consistency for testing muscle trigger points.

As indicated in a brochure entitled, "Pain and Soft Tissue Pathology Instruments", Pain Diagnostics and Thermography of Great Neck, N.Y. appears to be marketing what are referred to as pain and soft tissue pathology instruments. These instruments apparently utilize a structural column arrangement, possibly a spring biased plunger arrangement, which interconnects a probe end of the instrument to a pressure gauge. In use, the user places the probe end against the tissue to be tested and applies pressure by grasping the gauge housing and forcing the gauge housing toward the probe end, whereupon the pressure is indicated at the pressure gauge. The instrument does not include a pressure probe adapted for positioning at the end of a user's finger and, as a result, does not offer the small size and flexibility of a user's finger in getting at hard to reach places, such as the underside of one's jaw. The pressure gauge is also rigidly attached to the pressure probe which further reduces the flexibility of the instrument.

The present invention solves many of the problems associated with existing algometer devices.

SUMMARY OF THE INVENTION

The present invention relates to a pressure algometer apparatus. The algometer apparatus includes pressure sensitive probe means for use in applying pressure to localized sites and for sensing the pressure applied to the localized sites. The pressure sensitive probe means includes hollow elastic housing means including surface means proximate a first end for receiving a distal end of a user's finger, the housing means including proximate a second end body tissue engaging surface means. Pressure responsive means is present for indicating pressure variations sensed by the pressure sensitive probe means. Interconnection means interconnects an interior of the elastic housing means to the pressure responsive means for providing air communication between the interior of the elastic housing means and the pressure responsive means.

The present invention also relates to an embodiment of the pressure algometer apparatus which includes transducer means for providing an electrical output signal indicative of the pressure sensed. This pressure responsive means is electrically interconnected to the pressure sensitive probe means for receiving the electrical output signal from the pressure sensitive probe means. The pressure responsive means includes readout means for indicating the pressure sensed by the pressure sensitive means. Means is further provided for electrical interconnection of the pressure algometer apparatus to a source of electrical energy.

The present invention further relates to a method for diagnosing muscle tissue pain and dysfunction. The method includes the steps of manually palpating muscle tissue trigger points using pressure sensitive means inserted over a user's finger and forming an air tight seal therewith, the pressure sensitive means being interconnected to, and in air communication with, pressure responsive means for indicating variations in pressure. The method includes a second step of observing the pressure indicated at the pressure responsive means and observing the patient's response to such pressure.

In the preferred method, the patient will be asked to indicate when they first start feeling pain as opposed to pressure. The user will then gradually increase the amount of pressure applied until the patient indicates they feel pain as opposed to only pressure. The user will typically observe the patient for any outward signs of pain; e.g., flinch, expression, etc.

In the first embodiment, the present invention provides an all mechanical pressure algometer apparatus which is easy to use and yet relatively accurate. In addition, the invention provides a pressure algometer apparatus which is relatively inexpensive. The pressure algometer apparatus will, therefore, be an efficient screening device for use in this field. This embodiment also has many other advantages. First, the shape and firmness of the pressure sensitive probe means of the pressure algometer is such that it effectively serves as an extension on one's finger. The relatively small size and flexibility of a user's finger also make the invention particularly useful for getting at hard to reach places such as the underside of one's jaw. Moreover, the pressure sensitive probe portion of the pressure algometer is deformable as to conform to the surface of the tissue being tested. The soft, deformable nature of the probe portion also reduces the likelihood that the probe portion itself will induce additional pain. Finally, the probe portion of the mechanical algometer is preferably covered by and retained at the distal end of the user's finger by a throw away retainer member such as a finger cot. This makes use of the pressure algometer of the present invention extremely sanitary. However, the numbers obtained through the mechanical algometer are expressed in pounds per square inch (PSI). Since these numbers are relative due to the variable geometry of the individual finger, absolute calibration is difficult.

The second embodiment of the invention can be absolutely calibrated because it employs a tissue engaging surface of constant geometry and relies on an electronic transducer, as opposed to air or gas pressure. This version of the invention may be somewhat more expensive and due to its increased accuracy, will probably be used mostly in a clinic setting. In the embodiments of this invention wherein a portable battery supply is provided, the device will be readily portable.

These and various other advantages and features of novelty which characterize the present invention are pointed out with particularity in the claims annexed hereto and forming a part hereof. However, for a better understanding of the invention, its advantages and objects attained by its use, reference should be had to the drawings, which form a further part hereof, and to the accompanying descriptive matter, in which there is illustrated and described a preferred embodiment of the invention.

BRIEF DESCRIPTION OF THE DRAWINGS

In the drawings, in which like reference numerals indicate corresponding parts throughout, FIG. 1 is a perspective view of one embodiment of a pressure algometer positioned at the distal end of a user's finger by use of finger cot in accordance with the principles of the present invention;

FIG. 2 is an enlarged partial cross-sectional view of the embodiment shown in FIG. 1;

FIG. 3 is a perspective view of one embodiment of a pressure sensitive probe member in accordance with the principles of the present invention.

FIG. 4 is a block diagram of a second embodiment of a pressure algometer apparatus in accordance with the principles of the present invention;

FIG. 5 is a perspective view of the embodiment shown in FIG. 4;

FIG. 6 is a schematic of the embodiment shown in FIG. 5; and

FIG. 7 is a schematic of one embodiment of a possible power supply for the embodiments shown in FIGS. 4 through 6.

DETAILED DESCRIPTION OF A PREFERRED EMBODIMENT

Illustrated in FIGS. 1 through 3, is a first embodiment of an algometer apparatus, generally referred to by the reference numeral 20, in accordance with the principles of the present invention. In the embodiment shown, the algometer apparatus 20 includes a resilient deformable, one-piece, integrally molded, plastic bladder member which functions as a pressure sensitive probe member 22. The pressure sensitive probe member is deformable but maintains its shape when not under pressure. The probe member has a first end surface providing a muscle tissue engaging surface 24 similar to a distal end of a user's finger and a second end surface providing a finger engaging surface 26 being configured and contoured for receiving a distal end surface 28 of a user's finger. In the embodiment shown, the surface 26 has a generally concave shape inversely similar to the distal end surface 28 of a user's finger for receiving the user's finger such that the user's finger uniformly abuts the surface 26 when pressure is applied. The balloon-like probe member 22 is configured to closely approximate and standardize the surface area, shape and firmness of a distal end portion of an index finger. The probe member 22 is interconnected to a 0 to 3 pound per square inch (PSI) low pressure diaphragm gauge by a length of vinyl tubing 42. As illustrated, the tubing 42 is interconnected to an interior area (cavity) 44 of the probe member 22 by a metal section of tubing 46.

In use, the probe member 22 is preferably retained at the distal end portion 28 of the user's finger 30 by a flexible tubular piece of material 32, such as a finger cot or the like, open at one end 34 for insertion of the user's finger 30 and closed at the other end 36.

As illustrated by the arrows 48, when the distal end portion 28 of the user's finger 30 is forced against the end surface 26 of the probe member 22, air, as generally illustrated by the arrows 48, is forced into the tubing 46 as the probe member 22 deforms and the interior area 44 decreases. The pressure responsive, low pressure diaphragm gauge 40 then provides a readout of the pressure variations created in the interior area 44 of the probe member 22. The probe member 22 is preferably configured such that the user's finger 30 does not hit the end surface 24 when pressure within normal operating ranges is applied.

In the preferred embodiment, the probe member 22 is made by dipping an aluminum mold in Iasco Vinyl Dispersion Number 60 Plastisol. After curing, the mold is removed by cutting the bladder member 22, and then resealing with cyclohexanone solvent.

In use, a user positions the probe member 22 at the distal end surface 28 of the index finger 30 and then inserts the index finger 30 into the tubular material 32 so as to facilitate retention of the probe member 22 proximate the distal end surface 28 of the index finger 30. A user then manually palpates muscle tissue trigger points using the probe member 22 which functions as a pressure sensitive device. The user typically will proceed by applying sufficient pressure against a muscle trigger point by forcing the index finger 30 against the end surface 26 of the probe member 22 such that the patient can sense the pressure but normally will not sense any pain. The user then gradually increases the amount of pressure applied until the patient reports feeling even the slightest pain. The user then observes the pressure readout indicated at the low pressure diaphragm gauge which serves as a pressure responsive device. This is then recorded as the pain threshold. If no pain threshold is illicited from the patient, the top end of the pressure gauge scale reading, roughly 1.0 pounds per inch, is recorded. After a predetermined interval; e.g., 5 seconds, the process might be repeated at the same trigger point. This process is repeated at other trigger points as desired. The same patient might then be so evaluated by a second user after a predetermined time; e.g., 5 minutes, so as to provide comparison results. It will be appreciated that the specific pressure utilized will vary.

Typically, the readout obtained is expressed in PSI and is relative, since the variable geometry of the user's finger makes absolute calibration difficult. As previously discussed, however, the present invention is particularly useful for getting at hard to reach places and is relatively inexpensive and entirely mechanical, so as to serve as a good screening device for field use as well as in the hospital facility. It will be appreciated that the present invention has numerous applications other than diagnosis of muscle pain or tenderness; e.g., diagnosis of joint capsulization, tissue compliance, sports medicine applications, etc.

Illustrated in FIGS. 4-7 is a second embodiment of an algometer apparatus, generally referred to by the reference numeral 50, in accordance with the principles of the present invention. The algometer apparatus 50 shown comprises a hand held pressure transducer device 52, supporting bridge electronics 49 for receiving electrical input signals from the hand held pressure transducer device 52, and an amplifier/meter circuitry arrangement 54 electrically interconnected to the bridge electronics 49 by a suitable electrical interconnection 53. The supporting bridge electronics 49 and the amplifier/meter circuitry 54 are disposed in a housing 55. The transducer 52 includes a stainless steel bar 56 mounted in a housing 51. A Kistler/Morse semiconductor strain gauge sensor cartridge 58 is mounted on the stainless steel bar 56 by suitable fasteners such as threaded screws 47 so as to sense any deflections of the bar 56. The supporting bridge electronics 49 located in housing 55 are electrically interconnected to the strain gauge sensor cartridge 58 by an electrical cord 57. The two resistors of the semiconductor strain gauge sensor cartridge 58 and the two resistors of the supporting bridge electronics 49 cooperate to provide a bridge function. The electrical interconnection 53 is slidably interconnected to a ten turn (10t) trim resistor so as to enable balancing of the bridge when in a neutral or unstressed state. When the bar 56 is displaced from its neutral state, the bridge function will become unbalanced and a corresponding signal value will be sent to the amplifier/meter circuitry 54 which in turn will output a corresponding signal to the meter 70, causing movement of the meter's pointer. As illustrated in FIG. 5, the steel bar 56 is mounted in the housing 51 so as to be secured against movement at a first end 56a and yet have a free end 56b. Interconnected to the steel bar 56 proximate the free end 56b is a plastic, lightweight, cylindrical probe member 59 oriented at 90° with respect to the housing 51. The probe member 59 is preferably lightweight such that the algometer readout is not affected by orientation of the housing 51. The probe member 59 has a contoured, curved end surface 60 for engaging the localized area of the patient being tested. The user grasps the housing 51 and forces the end surface 60 of the probe member 59 against the muscle trigger point being tested. As the user applies force, the probe member 59 displaces the free end 56b of the steel rod 56. The semi-conductor strain gauge sensor 58 then senses this displacement and a corresponding signal is transmitted via the electrical cord 57 to the bridge electronics 49 and then to the amplifier/meter circuitry 54 ultimately resulting in a corresponding readout at the meter 70. A stop or movement limiter 62 might be provided for limiting movement of the steel rod member 56. The sensitivity of the semiconductor sensor cartridge 58 is such that it can detect extremely small deflections of the stainless bar 56 many times under the elastic limits of the stainless steel bar. The amplifier meter arrangement 54 includes a one-milliamper meter 70 as a pressure indicator device which is driven by an operational amplifier 72. Both the pressure transducer arrangement 52 and its supporting bridge electronics 49, as well as the amplifier/meter arrangement 54 are battery powered, making for a readily portable, easy to use pressure measuring device. Illustrated in FIG. 7, a dual battery arrangement 74 is used to power the amplifier/meter arrangement while a separate battery arrangement 76 is used for the energy supply of the semiconductor sensor cartridge 58 and its supporting bridge electronics 49. In the preferred embodiment, the batteries are also located in the housing 55. The housing 55 is shown further including an on/off switch 80, a meter zero control 82, a meter span control 84, and the meter 70.

A miniature load cell might be used for the tranducer so as to provide a more linear output. However, it is anticipated that such an approach would result in a much greater cost. It will be appreciated that numerous types of strain gauge devices might be utilized in keeping with the principles of the invention.

This embodiment can be absolutely calibrated because the probe member 59 muscle tissue engaging surface is of substantially constant geometry. Moreover, it is electronic and relies on a transducer to sense the pressure applied. This embodiment, although somewhat more expensive, is more accurate and will probably be used mostly in a clinical setting.

It is to be understood, however, that even though numerous characteristics and advantages of the invention have been set forth in the foregoing description, together with details of the structure and function of the invention, the disclosure is illustrative only and changes may be made in detail, especially in matters of shape, size and arrangement of parts, within the principles of the invention, to the full extent indicated by the broad general meaning of the terms in which the appended claims are expressed.

What is claimed is:

1. A pressure algometer apparatus, comprising:
   (a) pressure sensitive probe means for sensing variations in pressure applied to a localized site on a patient's body, the probe means comprising a hollow, air tight bladder having the shape and firmness of a distal end portion of a user's finger and including a contoured concave surface for receiving a distal end surface of a user's finger and an opposing surface for engaging the localized site on the patient's body, the bladder maintaining its shape when not subjected to pressure from the user's finger pressing on the bladder;
   (b) pressure responsive means for indicating pressure variations sensed by the pressure sensitive probe means; and
   (c) flexible hollow tubing means interconnecting an interior of the hollow bladder to the pressure responsive means for providing air communication between the interior of the hollow bladder and the pressure responsive means.

2. An apparatus in accordance with claim 1, wherein the pressure responsive means includes pressure gauge means for providing a pressure readout.

3. An apparatus in accordance with claim 1, wherein the bladder comprises a one-piece, deformable, integrally molded plastic member.

4. An apparatus in accordance with claim 2, wherein the pressure gauge means includes a diaphragm gauge device interconnected to the flexible hollow tubing means.

* * * * *

UNITED STATES PATENT AND TRADEMARK OFFICE
CERTIFICATE OF CORRECTION

PATENT NO. : 4,768,521

DATED : September 6, 1988

INVENTOR(S) : Schiffman et al.

It is certified that error appears in the above-identified patent and that said Letters Patent is hereby corrected as shown below:

Title Page, Column 1, Under References Cited, Line 6, "Romanooskaya" should be --Romanovskaya--.

Column 3, Line 40, "." should be --;--.

Column 5, Line 61, after "stainless" insert --steel--.

Column 5, Line 63, "one-milliamper" should be --one-milliampere--.

Signed and Sealed this

Twenty-first Day of February, 1989

Attest:

DONALD J. QUIGG

*Attesting Officer*     *Commissioner of Patents and Trademarks*